(12) United States Patent
Frith

(10) Patent No.: US 9,345,868 B2
(45) Date of Patent: May 24, 2016

(54) OINTMENT APPLICATOR

(71) Applicant: Sherry Frith, Bakersfield, CA (US)

(72) Inventor: Sherry Frith, Bakersfield, CA (US)

(*) Notice: Subject to any disclaimer, the term of this patent is extended or adjusted under 35 U.S.C. 154(b) by 227 days.

(21) Appl. No.: 14/164,037

(22) Filed: Jan. 24, 2014

(65) Prior Publication Data

US 2014/0207089 A1   Jul. 24, 2014

Related U.S. Application Data

(60) Provisional application No. 61/756,433, filed on Jan. 24, 2013.

(51) Int. Cl.
*A61M 35/00* (2006.01)

(52) U.S. Cl.
CPC .................................. *A61M 35/003* (2013.01)

(58) Field of Classification Search
CPC .. A61M 35/00; A61M 35/003; A61M 35/006
See application file for complete search history.

(56) References Cited

U.S. PATENT DOCUMENTS

| | | | | |
|---|---|---|---|---|
| 3,683,915 A * | 8/1972 | Voss | ..................... | A61F 13/2051 604/14 |
| 4,421,504 A * | 12/1983 | Kline | .................. | A61M 31/007 604/12 |
| 4,690,671 A * | 9/1987 | Coleman | .................. | A61F 13/26 604/12 |
| 5,795,320 A * | 8/1998 | Nielsen | ............... | A61M 31/007 604/11 |
| 6,368,442 B1 * | 4/2002 | Linares | ............... | A61F 13/2085 156/198 |
| 2010/0114071 A1 * | 5/2010 | Braunagel | ........... | A61M 3/0262 604/540 |

* cited by examiner

*Primary Examiner* — Susan Su

(74) *Attorney, Agent, or Firm* — Matthew C. McCartney, Esq.; Eastman & McCartney LLP

(57) ABSTRACT

The present invention provides an anti-microbial or anti-bacterial treated soft ointment applicator that is used to apply ointment or cream on babies. The ointment applicator with a soft and flexible tapered tip in the present invention can be applied along the curvature of a baby's body without causing harm to baby's sensitive and delicate skin. The present invention provides an anti-microbial or anti-bacterial treated ointment applicator either coated with, or homogeneously manufactured with, such anti-microbial or anti-bacterial protection. In addition, the present invention includes a reservoir filled with a cleaning solution where the ointment applicator is cleaned and stored sterile. Therefore, the present invention helps not only with easy application of ointments or creams on the delicate skin, but also to protect the babies' skin from infection, microbial or bacterial contamination, or any further skin irritations caused from cross contamination between the applicator, ointment or cream, and the babies' skin.

17 Claims, 4 Drawing Sheets

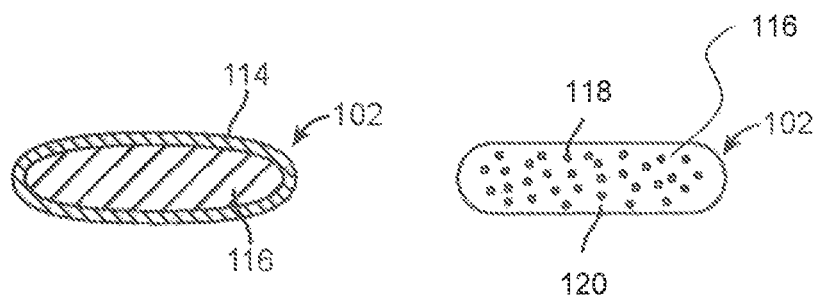

OINTMENT APPLICATOR

RELATED APPLICATIONS

The present application claims the benefit of priority to U.S. Provisional Patent Application Ser. No. 61/756,433, entitled "Ointment Applicator," filed Jan. 24, 2013.

FIELD OF THE INVENTION

The present invention pertains generally to an applicator that is used to apply baby ointment or baby cream on the delicate skin of babies. The present invention is more particularly, though not exclusively, useful as an applicator equipped with a soft and flexible tip, and specifically treated with an anti-microbial or anti-bacterial component to avoid any microbial or bacterial contamination on the applicator, further limiting spread of the contamination to the ointment or cream products, as well as to the baby's skin. In addition, the present invention provides a reservoir filled with a cleaning solution for disinfecting and storage of the ointment applicator to keep the applicator sterile after and between uses.

BACKGROUND OF THE INVENTION

Cosmetic applicators have been used for years to scoop and spread cosmetics on the skin of people. It has been known that a cosmetic product that is good for people's skin is also good breeding ground for microorganisms; bacteria and fungus. Excessive amounts of bacteria and fungus can affect the cosmetic products in a number of ways; causing odors, destabilizing the emulsion, and causing color changes. Such microorganisms can also affect the consumer negatively in ways ranging from harmless itching of the skin to serious infection, and even blindness if the product is used around the eyes. Specifically, it has been widely known that sticking fingers inside cosmetic products causes contamination of the cosmetic products. Therefore, people have been recommended to avoid sticking their fingers inside cosmetic products, but to use cosmetic applicators to scoop out the cosmetic products.

In addition to the cosmetic products for adults, babies are often in need of ointment or cream for their diaper rash, infant acne, eczema, and other skin irritations. For the treatment of such skin irritations of babies, or just for addition of moisture on the babies' skin, it has been recommended for people in care of such babies to use an applicator, in order to apply any ointment or cream on babies to avoid any bacterial contamination. It is also recommended to completely clean the applicators with a cleansing liquid or soap, and to place it on a clean surface. However, the process of constantly cleaning and re-sterilizing the applicator, along with storing it on a clean surface, is not easy for many users. As a result, currently available applicators used for application of ointment or cream tend to become contaminated, and spread that contamination to the ointment or cream products. The result is an increased risk of causing irritation or infection on the skin being treated with contaminated ointment and/or a contaminated applicator.

Even though various types of applicators have been developed and used for scooping out cosmetic products of cream types or ointments, no applicators with a flexible tip sufficiently soft for spreading and application of the products on the delicate skin of babies have been developed. Since baby's skin is sensitive and delicate, scratches, infection or another skin irritation can be caused from application of ointment or cream, if such ointment or cream is applied by a rigid or porous applicator.

In light of the above, it would be advantageous to provide an ointment applicator treated with anti-microbial or anti-bacterial materials to reduce any cross-contamination between the user's fingers, ointment or cream container, the applicator, and the baby's skin where the ointment or cream is applied. It would also be advantageous to provide an ointment applicator which is equipped with a soft and flexible tip to prevent any harm which has typically/heretofore been caused on the babies' skin from the application of ointment or cream by currently available rigid applicators. It would be further advantageous to provide an ointment applicator which can be completely cleaned after each use and kept sterile between uses.

SUMMARY OF THE INVENTION

The present invention includes an anti-microbial or anti-bacterial treated soft ointment applicator that is used to apply baby ointment or baby cream on the delicate skin of babies. This invention provides an ointment applicator with a soft and flexible by that can be applied along the curvature of a baby's body without causing harm to baby's sensitive and delicate skin. The present invention is advantageous in providing an anti-microbial or anti-bacterial protection by having an ointment applicator which is either coated with, or homogeneously manufactured with, such anti-microbial or anti-bacterial additive materials, in addition, in a preferred embodiment, the present invention provides a reservoir filled with a cleaning solution where the ointment applicator is cleaned and stored in a sterile environment. Therefore, the present invention helps not only with easy application of ointments or creams on the babies, but also to protect the babies' sensitive and delicate skin from infection, microbial or bacterial contamination, or any further skin irritations. The present invention may also be used for elderly people or people having a sensitive skin.

BRIEF DESCRIPTION OF THE DRAWING

The nature, objects, and advantages of the present invention will become more apparent to those skilled in the art after considering the following detailed description in connection with the accompanying drawings, in which like reference numerals designate like parts throughout, and wherein:

FIG. 4 is a cross-sectional view taken along line 4-4 of the ointment applicator shown in FIG. 3, illustrating an anti-microbial or anti-bacterial top coating applied throughout the entire surface of the ointment applicator;

FIG. 5 is a cross-sectional view taken along line 4-4 of the ointment applicator shown in FIG. 3, illustrating an alternative method of anti-microbial or anti-bacterial protection homogeneously built into the ointment applicator;

DETAILED DESCRIPTION OF THE INVENTION

Figure 1:
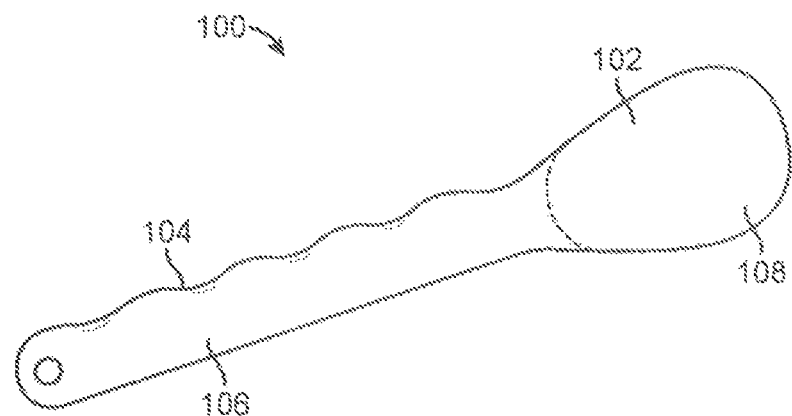
FIG. 1 is a top plan view of the ointment applicator comprising a spreader head, a grip and a handle.

Referring initially to FIG. 1, the present invention discloses an ointment applicator 100 for application of baby ointment or baby cream on babies. The ointment applicator 100 includes a spreader head 102 connected to a handle 106. The spreader head 102 also has a tapered tip 108. The ointment applicator 100 of the present invention is made of silicone or similar soft material such that the ointment applicator 100 does not irritate delicate and sensitive babies' skin when it is applied. When in use, ointment or cream is applied to the surface of the spreader head 102 to enable the user to spread the ointment onto the surface of a recipient, such as a baby. To allow for easier application and to prevent a user's hand from slipping during application of ointment or cream, the ointment applicator 100 adopts a grip 104.

Figure 2:
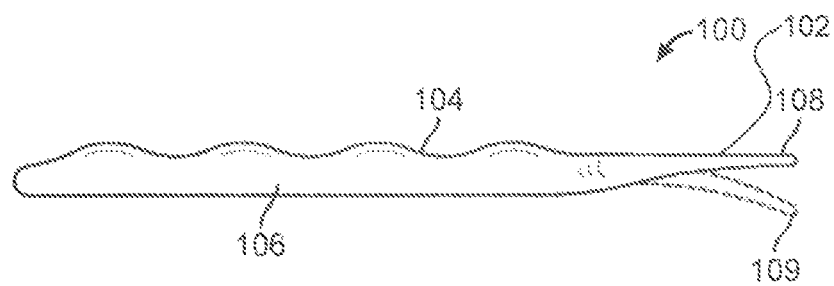
FIG. 2 is a side view of the ointment applicator illustrating a tapered and flexible tip.

As shown in the side view of the ointment applicator 100 of the present invention depicted in FIG. 2, the tapered tip 108 tapers and is made of soft and flexible material that can be flexed as depicted in dashed lines 109, and thus easily conformable to the curved body parts of babies, without causing any irritation on the sensitive babies' skin. In an embodiment, the spreader head 102, grip 104, handle 106 and tapered tip 108 can all be manufactured with a uniform material, such as silicone. The ointment applicator 100 can be manufactured by a process of injection molding or any other plastics molding process known in the art.

In addition, with an aid of the grip 104 on the side of the handle 106, the ointment applicator 100 of the present invention helps the users easily apply the ointment or cream on the baby's skin, along with the curvature of a baby's body, without worries of the hand's being slipped off the ointment applicator 100 during application. With an aid of the grip 104, a user can effectively grip the handle even when his or her hands are wet. In addition, the grip 104 enables the user to use the ointment applicator 100 without worry of getting the ointment or cream on the user's hands, and without concerns of cross-contamination of the ointment or cream container.

Figure 3:
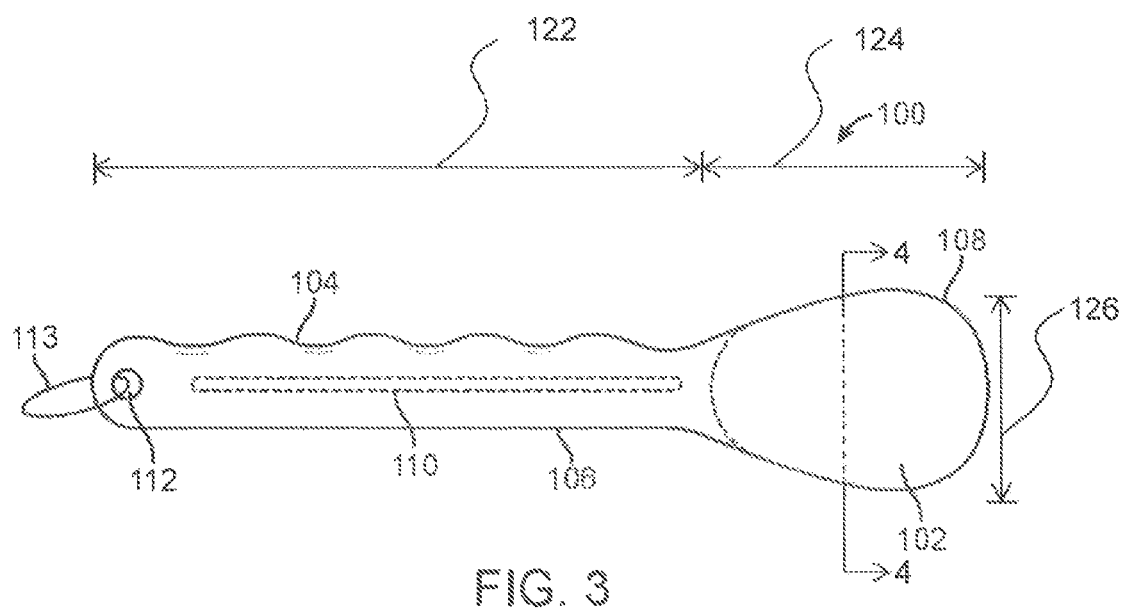
FIG. 3 is a top plan view of the ointment applicator equipped with a stiffening rod (shown in dashed lines) inside, illustrating suggested dimensions.

FIG. 3 illustrates a top plan view of the ointment applicator 100 of the present invention equipped with a stiffening rod 110 (shown in dashed lines) embedded inside the handle 106. Even though the ointment applicator 100 of the present invention provides a soft and flexible tapered tip 108, the handle 106 is equipped with a stiffening rod 110, for easy control of the soft and flexible tapered tip 108. By adopting a stiffening rod 110 which maintains the handle straight and rigid, the pressure from the users hand can be properly adjusted and applied to the handle 106, resulting in desirable and proper application of the ointment or cream, while ensuring a delicate application on the babies' skin. In addition, a hole 112 may be used in conjunction with a string or a strap 113 such that the ointment applicator 100 can be hung on the wall through the string or strap 113, when not in use. Furthermore, FIG. 3 illustrates suggested dimensions for the preferred embodiment of the present invention where the handle 106 has a length 122 and the spreader head has a length 124 and a width 126. In a preferred embodiment of the ointment applicator 100 of the present invention, the length 122 of the spreader head 102 is 2¼" and the width 126 is 1½" in its width, while the length 122 of the handle 106 is 6". Such dimensions are suggested as one of the examples for the dimensions that would be adopted for the embodiments of the present invention. The suggested dimensions were based upon consideration of an average sized adult hand and the usual amount of ointment or cream applied to the babies. As an alternative embodiment, the ointment applicator 100 of the present invention can also be used for elderly people or people generally having sensitive skin. Therefore, the ointment applicator 100 may be formed to have different dimensions, such as a bigger spreader head 102, a bigger grip 104, and handle 106, may also be considered for the use on such people, and are fully contemplated herein.

Now referring to FIG. 4, a cross-sectional view taken along line 4-4 of the ointment applicator shown in FIG. 3, treated with anti-microbial or anti-bacterial coating, is depicted. As shown in FIG. 4, the ointment applicator 100 of the present invention is made of silicone or similar soft material 116 such that the ointment applicator 100 does not irritate delicate and sensitive babies' skin. As one of the methods for treatment of anti-microbial or anti-bacterial component on the ointment applicator 100, the surface of the ointment applicator 100 is coated with a coated layer 114 of material having anti-microbial or anti-bacterial additives. When so coated, the entire surface of the ointment applicator 100 is protected from microbial or bacterial contamination.

FIG. 5 depicts a cross-sectional view taken along line 4-4 of the ointment applicator shown in FIG. 3, with an alternative method for treatment of anti-microbial or anti-bacterial component. As shown in FIG. 5, anti-microbial or anti-bacterial additive particles 118 can also be homogeneously distributed throughout the entire product matrix of the ointment applicator 100. In this embodiment, during the manufacturing process, anti-microbial or anti-bacterial material is nixed with the primary soft material 116, such as silicone, resulting in an ointment applicator 100 that has anti-microbial or anti-bacterial particles 118 that are evenly dispersed within the silicone or similar soft material particles 120. The ointment applicator 100 manufactured in such a manner has continuous and homogeneous anti-microbial protection both internally and on the surface. In another embodiment, only the spreader head 104 and tapered tip 108 have anti-bacterial additive particles homogeneously distributed throughout allowing the handle 106 and grip 104 to be manufactured from a uniform cheaper material.

Figure 6:
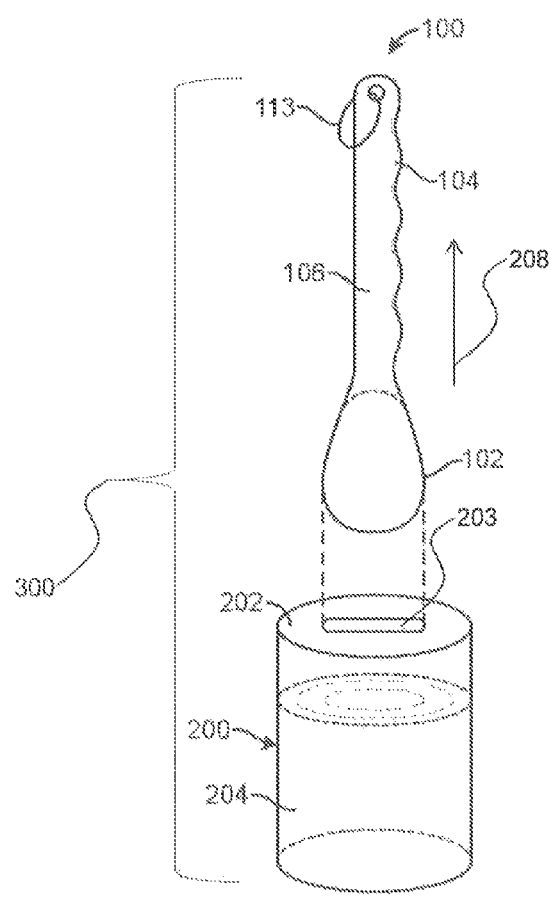
FIG. 6 is a perspective view of the ointment applicator when it is removed from the reservoir to be used for application of ointment or cream.
Figure 7:
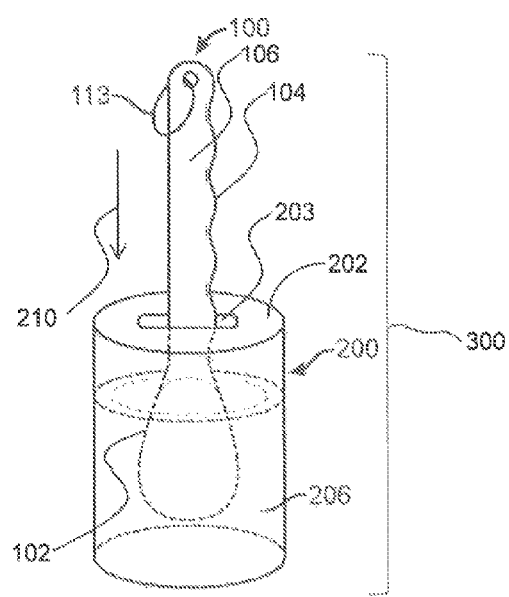
FIG. 7 is a perspective view of the ointment applicator when it is inserted to the reservoir filled with a cleaning solution for cleansing the ointment applicator after each use and for storage of the ointment applicator when not in use.

FIGS. 6 and 7 are perspective views of a self-cleaning ointment applicator 300 that consists of an ointment applicator 100 and a reservoir 200. The reservoir 200 has a lid 202 with an opening 203. As can be seen in FIG. 6, the opening 203 of the lid 202 is sized to receive the spreader head 102 of the ointment applicator 100 such that the ointment applicator can be moved in use direction 208 to remove the ointment applicator 100 from the reservoir 200 for use. As the ointment applicator 100 is removed from the reservoir 200, it is cleaned by cleaning solution 204 stored within the reservoir 200. Once removed from the reservoir 200, the ointment applicator 100 can be used to apply ointment or cream as needed.

As can be seen in FIG. 7, a user can replace the cleaning solution 204 with a new cleaning solution 206. After each use, the ointment applicator 100 is moved in stored direction 210 such that the ointment applicator 100 is inserted into the reservoir 200, through the opening 203 of lid 202 of the reservoir 200. When the ointment applicator 100 is inserted through the opening 203, its spreader head 102 is completely submerged in the new cleaning solution 206 allowing any remaining ointment on the spreader head 102 to be cleaned by the new cleaving solution 206. In addition, after cleaning of the ointment applicator 100, the user can store the ointment applicator 100 within the reservoir 200, with the spreader head 102 of the ointment applicator 100 submerged into the new cleaning solution 206, until the next use. While stored within this reservoir 200, the ointment applicator 100 is kept sterile, without microbial or bacterial contamination, between uses. It is optimal to regularly replace the cleaning solution during the course of storage of the ointment applicator 100.

As an alternative embodiment, the ointment applicator 100 of the present invention can also be used for elderly people, people having a sensitive skin, or any people in need of a soft and flexible applicator for ointment, cream or any other cosmetic products. The present invention may also be used to provide anti-microbial or anti-bacterial treated applicators which can be cleaned and kept sterile after and between uses, to such elderly people, people having a sensitive skin, or any people in need of the ointment applicators disclosed in the present invention.

While there have been shown what are presently considered to be preferred embodiments of the present invention, it will be apparent to those skilled in the art that various changes and modifications can be made herein without departing from the scope and spirit of the invention.

I claim:

1. An ointment applicator, comprising:
a handle terminating in a spreader head with a tapered tip wherein said handle, said spreader head and said tapered tip are coated with one or more layers of material having anti-bacterial additives, a stiffening rod embedded in said handle, and a hole through said handle wherein a strap passes through said hole.

2. The ointment applicator of claim 1, wherein said handle has a grip.

3. The ointment applicator of claim 1, wherein said tapered tip is flexible.

4. The ointment applicator of claim 1 wherein said ointment applicator is made from a soft material.

5. An ointment applicator, comprising:
a handle terminating in a spreader head with a tapered tip wherein said handle, said spreader head and said tapered tip each has anti-bacterial additive particles homogeneously distributed throughout said handle, said spreader head and said tapered tip.

6. The ointment applicator of claim 5, wherein said handle has a grip.

7. The ointment applicator of claim 5, wherein said tapered tip is flexible.

8. The ointment applicator of claim 5 further comprising a stiffening rod embedded in said handle.

9. The ointment applicator of claim 5 wherein said anti-bacterial additive particles are mixed with a primary soft material.

10. The ointment applicator of claim 5 further comprising a hole through said handle wherein a strap passes through said hole.

11. A self-cleaning kit comprising:
an ointment applicator having a handle terminating in a spreader head with a tapered tip, wherein said handle, said spreader head and said tapered tip each have anti-bacterial additives on an entire surface thereof; and
a reservoir having a lid with an opening sized to receive said spreader head of said ointment applicator.

12. The self-cleaning kit of claim 11 wherein said anti-bacterial additives is a coated layer applied to said handle, said spreader head, and said tapered tip.

13. The self-cleaning kit of claim 11, wherein said handle has a grip and wherein said tapered tip is flexible.

14. The self-cleaning kit of claim 11 further comprising a stiffening rod embedded in said handle.

15. The self-cleaning kit of claim 11 wherein said anti-bacterial additives comprise particles homogeneously distributed throughout said handle, said spreader head and said tapered tip.

16. The self-cleaning kit of claim 15, wherein said handle has a grip and wherein said tapered tip is flexible.

17. The self-cleaning kit of claim 16 further comprising a stiffening rod embedded in said handle.

* * * * *